United States Patent
Kitano et al.

(10) Patent No.: US 9,434,927 B2
(45) Date of Patent: Sep. 6, 2016

(54) METHOD FOR MANUFACTURING CELL CULTURE SUBSTRATE

(75) Inventors: Hiromi Kitano, Toyama (JP);
Yoshiyuki Saruwatari, Kashiwara (JP);
Kazuyoshi Matsuoka, Kashiwara (JP)

(73) Assignee: OSAKA ORGANIC CHEMICAL INDUSTRY LTD., Osaka (JP)

( * ) Notice: Subject to any disclaimer, the term of this patent is extended or adjusted under 35 U.S.C. 154(b) by 281 days.

(21) Appl. No.: 13/820,037

(22) PCT Filed: Aug. 30, 2011

(86) PCT No.: PCT/JP2011/069510
§ 371 (c)(1),
(2), (4) Date: May 17, 2013

(87) PCT Pub. No.: WO2012/029731
PCT Pub. Date: Mar. 8, 2012

(65) Prior Publication Data
US 2013/0224861 A1    Aug. 29, 2013

(30) Foreign Application Priority Data

Aug. 31, 2010 (JP) ................................ 2010-194911

(51) Int. Cl.
*C12N 5/071* (2010.01)
*C12N 5/00* (2006.01)

(52) U.S. Cl.
CPC ........... *C12N 5/0686* (2013.01); *C12N 5/0068* (2013.01); *C12N 2533/30* (2013.01)

(58) Field of Classification Search
CPC . C12N 2535/10; C12N 2539/10; G03F 7/26; G03F 7/085; G03F 7/038
USPC ....... 522/1, 2, 113, 114, 116, 117, 120, 126, 522/129, 130, 149, 150, 151, 152, 153, 173, 522/178, 182; 435/402
See application file for complete search history.

(56) References Cited

U.S. PATENT DOCUMENTS

2005/0279730 A1* 12/2005 Miyake ................. B01L 3/0268
216/41

FOREIGN PATENT DOCUMENTS

| JP | 2-84174 A | 3/1990 |
| JP | 2003-82119 A | 3/2003 |
| JP | 2005-52011 A | 3/2005 |
| JP | 2010-57745 A | 3/2010 |

OTHER PUBLICATIONS

International Search Report for PCT/JP2011/069510, mailing date of Nov. 15, 2011.
Office Action dated Aug. 18, 2015, issued in counterpart Japanese application No. 2012-531871 (4 pages).

* cited by examiner

*Primary Examiner* — Sanza McClendon
(74) *Attorney, Agent, or Firm* — Westerman, Hattori, Daniels & Adrian, LLP

(57) ABSTRACT

A method for manufacturing a cell culture substrate obtained by forming a coating layer of a polymer on the surface of a substrate, wherein the polymer is formed by polymerizing a monomer component containing a nitrogen atom-containing monomer represented by formula (I):

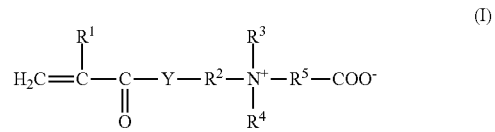

wherein $R^1$ is hydrogen atom or methyl group, $R^2$ is an alkylene group having 1 to 6 carbon atoms, each of $R^3$ and $R^4$ is independently an alkyl group having 1 to 4 carbon atoms, $R^5$ is an alkylene group having 1 to 4 carbon atoms, and Y is oxygen atom or —NH— group, includes irradiating the polymer with ion beam at a predetermined position of the coating layer of the polymer, to remove the coating layer of the polymer irradiated with the ion beam.

11 Claims, No Drawings

METHOD FOR MANUFACTURING CELL CULTURE SUBSTRATE

TECHNICAL FIELD

The present invention relates to a method for manufacturing a cell culture substrate. More particularly, the present invention relates to a method for manufacturing a cell culture substrate which can be suitably used in regenerating a cell having a shape corresponding to the shape of a tissue to be regenerated.

BACKGROUND ART

In recent years, expectations for regenerative medicine by cell culture using embryonic stem cells (ES cells), mesenchymal cells, induced pluripotent stem cells (iPS cells), progenitor cells, and the like aimed at differentiation and induction of various cells have been increasing. When cells are cultured, a medium made of a flat plate-shaped substrate has been generally used. As a material being able to be suitably used in this medium and having excellent biocompatibility, there has been proposed a medical material having a polymer brush on the surface of a substrate, the polymer brush being obtained by polymerizing a monomer composition containing N-methacryloyloxyethyl-N,N-dimethyl-ammonium-α-N-methylcarboxy-betaine (for example, see Patent Literature 1).

The above-mentioned medical material shows a small interaction with biological components such as proteins and blood cells, and is excellent in biocompatibility. If cells can be easily cultured in an arbitrary shape on the above-mentioned medical material, it is expected that such culture greatly contributes to regenerative medicine. However, a method for easily manufacturing a cell culture substrate which allows cells to be cultured in an arbitrary shape on the medical material has not yet been established. Therefore, development of such a method is in urgent need.

PRIOR ART DOCUMENTS

Patent Literature

Patent Literature 1: Japanese Unexamined Patent Publication No. 2010-57745

SUMMARY OF INVENTION

Problems to be Solved by the Invention

The present invention has been made in view of the above-mentioned prior art. An object of the present invention is to provide a method for manufacturing a growing substrate which enables easy manufacture of a cell culture substrate which allows cells to be cultured in an arbitrary shape.

Means for Solving the Problems

The present invention relates to:
(1) a method for manufacturing a cell culture substrate including a substrate and a coating layer of a polymer formed on the surface of the substrate, wherein the above-mentioned polymer is formed by polymerizing a monomer component containing a nitrogen atom-containing monomer represented by the formula (I):

[Chem. 1]

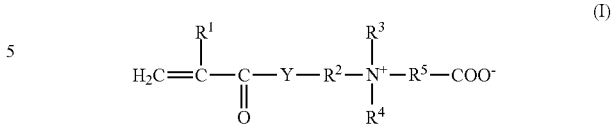

wherein $R^1$ is hydrogen atom or methyl group, $R^2$ is an alkylene group having 1 to 6 carbon atoms, each of $R^3$ and $R^4$ is independently an alkyl group having 1 to 4 carbon atoms, $R^5$ is an alkylene group having 1 to 4 carbon atoms, and Y is oxygen atom or —NH— group, comprising irradiating the above-mentioned coating layer of the polymer at a predetermined position with ion beam, to remove the coating layer of the polymer irradiated with the ion beam;

(2) the method for manufacturing a cell culture substrate according to the above (1), wherein the monomer component further contains at least one copolymerizable monomer selected from the group consisting of an alkyl (meth)acrylamide-based monomer, a polyoxyalkylene(meth)acrylate-based monomer, a sugar backbone-containing monomer, a phosphobetaine-based monomer and a sulfobetaine-based monomer;

(3) the method for manufacturing a cell culture substrate according to the above (1) or (2), wherein the coating layer of the polymer is formed by polymerizing the monomer component on the surface of the substrate; and (4) a cell culture substrate obtained by the method for manufacturing a cell culture substrate according to any one of the above (1) to (3).

Effects of the Invention

According to the method for manufacturing a cell culture substrate of the present invention, a cell culture substrate capable of culturing cells into an arbitrary shape can be easily manufactured.

MODES FOR CARRYING OUT THE INVENTION

As described above, the method for manufacturing a cell culture substrate of the present invention relates to a method for manufacturing a cell culture substrate including a substrate and a coating layer of a polymer formed on the surface of the substrate, wherein the polymer is formed by polymerizing a monomer component containing a nitrogen atom-containing monomer represented by the formula (I):

[Chem. 2]

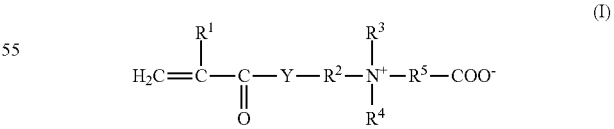

wherein $R^1$ is hydrogen atom or methyl group, $R^2$ is an alkylene group having 1 to 6 carbon atoms, each of $R^3$ and $R^4$ is independently an alkylene group having 1 to 4 carbon atoms, $R^5$ is an alkylene group having 1 to 4 carbon atoms, and Y is oxygen atom or —NH— group,
comprising irradiating the above-mentioned polymer at a predetermined position with ion beam, to remove the coating layer of the polymer irradiated with the ion beam.

One of major features of the present invention resides in that a polymer obtained by polymerizing a monomer component containing the nitrogen atom-containing monomer is used, and the above-mentioned coating layer of the polymer is irradiated at a predetermined position with ion beam. When the above-mentioned coating layer of the polymer is irradiated at a predetermined position with ion beam, since the polymer irradiated with ion beam is removed, a cell culture substrate having a coating pattern of a predetermined shape can be obtained. When cells are cultured by using this cell culture substrate, the cells are cultured at the position where the polymer is irradiated with ion beam because the polymer is not existed. In contrast, the cells are not cultured at the position where the polymer is not irradiated with ion beam because the polymer is existed. Therefore, cells can be cultured in a predetermined shape.

In the nitrogen atom-containing monomer represented by the formula (I), $R^1$ is hydrogen atom or methyl group.

$R^2$ is an alkylene group having 1 to 6 carbon atoms, preferably an alkylene group having 1 to 4 carbon atoms, more preferably an alkylene group having 1 or 2 carbon atoms, and further preferably an alkylene group having 2 carbon atoms. Specific examples of $R^2$ include methylene group, ethylene group, n-propylene group, isopropylene group, n-butylene group, isobutylene group and tert-butylene group, and the present invention is not limited only to those exemplified ones. Among the alkylene groups having 1 to 6 carbon atoms, methylene group and ethylene group are preferable, and ethylene group is more preferable.

Each of $R^3$ and $R^4$ is independently an alkyl group having 1 to 4 carbon atoms. The alkyl group having 1 to 4 carbon atoms includes, for example, methyl group, ethyl group, n-propyl group, isopropyl group, n-butyl group, isobutyl group, tert-butyl group and the like, and the present invention is not limited only to those exemplified ones. Among the alkyl groups having 1 to 4 carbon atoms, methyl group and ethyl group are preferable, and methyl group is more preferable.

$R^5$ is an alkylene group having 1 to 4 carbon atoms. The alkylene group having 1 to 4 carbon atoms includes, for example, methylene group, ethylene group, n-propylene group, isopropylene group, n-butylene group, isobutylene group, tert-butylene group and the like, and the present invention is not limited only to those exemplified ones. Among the alkylene groups having 1 to 4 carbon atoms, methylene group and ethylene group are preferable, and methylene group is more preferable.

Y is oxygen atom or —NH— group.

The nitrogen atom-containing monomer represented by the formula (I) has a concept which includes a hydrate. Accordingly, the concept of the nitrogen atom-containing monomer represented by the formula (I) encompasses not only the nitrogen atom-containing monomer represented by the formula (I) but also its hydrate such as its monohydrate.

The nitrogen atom-containing monomer represented by the formula (I) includes, for example, N-(meth)acryloyloxyethyl-N,N-dimethylammonium-α-N-methylcarboxy-betaine, N-(meth)acryloyloxypropyl-N,N-dimethylammonium-α-N-methyl-carboxybetaine, N-(meth)acryloylaminoethyl-N,N-dimethyl-ammonium-α-N-methylcarboxybetaine, N-(meth)acryloylaminopropyl-N,N-dimethyl-ammonium-α-N-methylcarboxybetaine and the like, and the present invention is not limited only to those exemplified ones. These nitrogen atom-containing monomers may be used alone or in combination of two or more kinds thereof. Incidentally, in the present specification, the term "(meth)acryloyl" means "acryloyl" and/or "methacryloyl".

In addition, N-methacryloyloxyethyl-N,N-dimethylammonium-α-N-methylcarboxybetaine can be easily prepared in high purity by a method as described in, for example, Japanese Unexamined Patent Publication No. Hei 9-95474, Japanese Unexamined Patent Publication No. Hei 9-95586, Japanese Unexamined Patent Publication No. Hei 11-222470, and the like.

The monomer component can be composed of only the nitrogen atom-containing monomer represented by the formula (I), or may contain a monomer capable of copolymerizing with the nitrogen atom-containing monomer (hereinafter the monomer is referred to as a "copolymerizable monomer").

The copolymerizable monomer includes, for example, an alkyl (meth)acrylamide-based monomer, a polyoxyalkylene (meth)acrylate-based monomer, a sugar backbone-containing monomer, a phosphobetaine-based monomer, a sulfobetaine-based monomer and the like, and these copolymerizable monomers may be used alone or in combination of two or more kinds thereof.

When the alkyl (meth)acrylamide-based monomer is incorporated into the monomer component, there is an advantage such that hydrolysis resistance of a polymer obtained can be improved. The alkyl (meth)acrylamide-based monomer includes, for example, N-methyl (meth)acrylamide. N-ethyl (meth)acrylamide, N-propyl (meth)acrylamide, N-isopropyl (meth)acrylamide, N-tert-butyl (meth)acrylamide, N-octyl (meth)acrylamide, N,N-dimethyl (meth)acrylamide, N,N-diethyl (meth)acrylamide and the like, and the present invention is not limited only to those exemplified ones. These alkyl (meth)acrylamide-based monomers may be used alone or in combination with two or more kinds thereof. Among these alkyl (meth)acrylamide-based monomers, N-propyl (meth)acrylamide and N-isopropyl (meth)acrylamide are preferable, N-isopropyl (meth)acrylamide is more preferable, and N-isopropyl acrylamide is further preferable. Incidentally, in the present specification, the term "(meth)acrylamide" means "acrylamide" and/or "methacrylamide".

The polyoxyalkylene(meth)acrylate-based monomer has a property for suppressing the adhesion of cells to a polymer obtained. The polyoxyalkylene(meth)acrylate-based monomer include, for example, polyoxyethylene(meth)acrylate-based monomers such as 2-methoxyethyl (meth)acrylate, 2-ethoxyethyl (meth)acrylate, methoxytriethyleneglycol (meth)acrylate, methoxytetraethyleneglycol(meth)acrylate, methoxypolyethyleneglycol(meth)acrylate and polyethyleneglycol mono(meth)acrylate; polyoxypropylene(meth)acrylate-based monomers such as 2-methoxy-2-methylethyl (meth)acrylate, 2-ethoxy-2-methylethyl (meth)acrylate, methoxytripropyleneglycol(meth)acrylate, methoxytetrapropyleneglycol(meth)acrylate, methoxypolypropyleneglycol(meth)acrylate and polypropyleneglycol mono (meth)acrylate and the like, and the present invention is not limited only to those exemplified ones. These polyoxyalkylene(meth)acrylate-based monomers may be used alone or in combination with two or more kinds thereof. Incidentally, in the present specification, the term "(meth)acrylate" means "acrylate" and/or "methacrylate".

The sugar backbone-containing monomer has a property for suppressing the adhesion of cells to a polymer obtained. The sugar backbone-containing monomer includes, for example, glucosylethyl (meth)acrylate, glucosylureaethyl (meth)acrylate and the like, and the present invention is not limited only to those exemplified ones. These sugar backbone-containing monomers may be used alone or in combination with two or more kinds thereof.

The phosphobetaine-based monomer has a property for suppressing the adhesion of cells to a polymer obtained. The phosphobetaine-based monomer includes, for example, 2-(meth)acryloyloxyethyl phosphocholine and the like, and the present invention is not limited only to those exemplified ones. These phosphobetaine-based monomers may be used alone or in combination with two or more kinds thereof.

The sulfobetaine-based monomer has a property for assisting the adhesion of cells to a polymer obtained. The sulfobetaine-based monomer includes, for example, N-(meth)acryloyloxyethyl-N,N-dimethylammonium-N-propylsulfobetaine and the like, and the present invention is not limited only to those exemplified ones. These sulfobetaine-based monomers may be used alone or in combination with two or more kinds thereof.

When the nitrogen atom-containing monomer is used together with the copolymerizable monomer, the ratio of the nitrogen atom-containing monomer to the copolymerizable monomer [nitrogen atom-containing monomer/copolymerizable monomer (mass ratio)] is preferably 1/99 or more, more preferably 3/97 or more, further preferably 5/95 or more, and particularly preferably 10/90 or more, from the viewpoint of improvement in biocompatibility. Also, from the viewpoint of sufficiently imparting properties of the copolymerizable monomer to a polymer, the above ratio is preferably 99/1 or less, more preferably 97/3 or less, further preferably 95/5 or less, and still further preferably 90/10 or less. Incidentally, the "biocompatibility" as used in the present specification means a property that protein is not easily adsorbed.

The monomer component used in the present invention contains the nitrogen atom-containing monomer, and the copolymerizable monomer as occasion demands. The monomer component may contain a monomer capable of copolymerizing with the nitrogen atom-containing monomer and the copolymerizable monomer so far as an object of the present invention is not hindered. Representative examples of the monomer capable of copolymerizing with the nitrogen atom-containing monomer and the copolymerizable monomer include a monomer having an unsaturated carbon-carbon double bond.

The monomer having an unsaturated carbon-carbon double bond includes, for example, a styrene-based monomer, a carboxylic acid ester-based monomer and the like, and the present invention is not limited only to those exemplified ones. These monomers capable of copolymerizing may be used alone or in combination with two or more kinds thereof.

When the styrene-based monomer is incorporated into the monomer component, there is an advantage such that heat resistance of a polymer obtained can be improved. The styrene-based monomer includes, for example, styrene, α-methylstyrene, α-hydroxystyrene, p-hydroxystyrene and the like, and the present invention is not limited only to those exemplified ones. These styrene-based monomers may be used alone or in combination with two or more kinds thereof.

When the carboxylic acid ester-based monomer is incorporated into the monomer component, there is an advantage such that lipophilicity of a polymer obtained can be improved. The carboxylic acid ester-based monomer includes, for example, alkyl (meth)acrylates, hydroxyalkyl (meth)acrylates, alkoxyalkyl (meth)acrylates and aralkyl (meth)acrylates, such as methyl (meth)acrylate, ethyl (meth)acrylate, propyl (meth)acrylate, n-butyl (meth)acrylate, isobutyl (meth)acrylate, tert-butyl (meth)acrylate, neopentyl (meth)acrylate, cyclohexyl (meth)acrylate, octyl (meth)acrylate, lauryl (meth)acrylate, stearyl (meth)acrylate, cetyl (meth)acrylate, ethylcarbitol(meth)acrylate, hydroxyethyl (meth)acrylate, hydroxypropyl (meth)acrylate, hydroxybutyl (meth)acrylate, methoxyethyl (meth)acrylate and methoxybutyl (meth)acrylate, as well as methyl itaconate, ethyl itaconate, vinyl acetate, vinyl propionate and the like, and the present invention is not limited only to those exemplified ones. These carboxylic acid ester-based monomers may be used alone or in combination with two or more kinds thereof.

When the monomer component is polymerized, it is preferred that a polymerization initiator is used. The polymerization initiator includes, for example, organic silane-based polymerization initiators such as (11-(2-bromo-2-methyl)propionyloxy)undecyltrichlorosilane, (4-(2-bromo-2-methylpropionyloxy)butyltrichlorosilane, (6-(2-bromo-2-methyl)propionyloxy)hexyltrichlorosilane and (8-(2-bromo-2-methyl)propionyloxy)octyltrichlorosilane; azo-based polymerization initiators such as azobisisobutyronitrile, azoisobutyronitrile, methyl azoisobutyrate and azobisdimethylvaleronitrile; peroxide-based polymerization initiators such as benzoyl peroxide; persulfate-based polymerization initiators such as potassium persulfate and ammonium persulfate, and the like, and the present invention is not limited only to those exemplified ones. These polymerization initiators may be used alone or in combination with two or more kinds thereof. Among them, the organic silane-based polymerization initiator is preferred.

When the organic silane-based polymerization initiator is used as a polymerization initiator, the organic silane-based polymerization initiator may be previously put on a substrate. When the organic silane-based polymerization initiator is previously put on a substrate, there is an advantage such that a coating layer of a polymer formed can be strongly fixed to the surface of a substrate.

The amount of the polymerization initiator is not particularly limited, and the amount is usually preferably 0.001 to 10 moles, more preferably 0.01 to 5 moles per 100 moles of the monomer component.

In addition, when the monomer component is polymerized, a chain transfer agent may be used in the present invention. The chain transfer agent can be usually used by mixing with the monomer component. The chain transfer agent includes, for example, mercaptan group-containing compounds such as lauryl mercaptan, dodecyl mercaptan and thioglycerol; inorganic salts such as sodium hypophosphite and sodium hydrogen sulfite; and the like, and the present invention is not limited only to those exemplified ones. These chain transfer agents may be used alone or in combination with two or more kinds thereof.

The amount of the chain transfer agent is not particularly limited, and the amount is usually about 0.01 to about 10 parts by mass per 100 parts by mass of the monomer component.

As a method for polymerizing the monomer component, there can be cited, for example, a solution polymerization method and the like, and the present invention is not limited only to those exemplified ones.

In addition, when the monomer component is polymerized, a coating layer can be formed on the surface of a substrate by polymerizing the monomer component on the surface of a substrate. When the monomer component is polymerized by the solution polymerization method, a coating layer can be formed on the surface of a substrate by, for example, dissolving the monomer component and a polymerization initiator in a solvent, and dipping the substrate in the resulting solution to polymerize the monomer component. Alternatively, a substrate having a coating layer of a polymer on its surface can also be produced by applying the monomer component to the surface of a substrate, followed by irradiation with light or heating, so that the monomer component is polymerized to form a coating film of the polymer on the surface of a substrate.

The solvent includes, for example, water; organic solvents such as alcohols such as methyl alcohol, ethyl alcohol, isopropyl alcohol, ethylene glycol and propylene glycol; ketones such as acetone and methyl ethyl ketone; ethers such as diethyl ether and tetrahydrofuran; aromatic hydrocarbon compounds such as benzene, toluene and xylene; aliphatic hydrocarbon compounds such as n-hexane; alicyclic hydrocarbon compounds such as cyclohexane; and acetic acid esters such as methyl acetate and ethyl acetate; and the like, and the present invention is not limited only to those exemplified ones. These solvents may be used alone or in combination with two or more kinds thereof. In addition, from the viewpoint of promoting the polymerization reaction of the monomer component smoothly, it is preferred that the organic solvent is previously deaerated with an inert gas such as nitrogen gas or argon gas.

It is preferred that the amount of the solvent is adjusted so that the concentration of the monomer component in a solution obtained by dissolving the monomer component in the solvent is usually about 10 to about 80% by mass.

In addition, when the monomer component is polymerized, a monovalent copper salt such as copper bromide or copper chloride, a polyvalent base such as bipyridyl or trisaminodiethylamine, or a free radical polymerization initiator such as ethyl-2-bromoisobutyrate may be allowed to coexist.

It is preferred that polymerization conditions such as polymerization temperature and polymerization period of time in the polymerization of the monomer component are appropriately controlled in accordance with the composition of the monomer component, the kind and amount of the polymerization initiator, and the like.

The atmosphere where the monomer component is polymerized is preferably an inert gas. The inert gas includes, for example, nitrogen gas, argon gas and the like, and the present invention is not limited only to those exemplified ones.

The completion of the polymerization reaction and the presence or absence of an unreacted monomer in the reaction system can be confirmed by, for example, a general analytical method such as gas chromatography.

In consideration of rheological characteristics of a polymer, or the balance of hydrophilic property and hydrophobic property of a polymer, the weight average molecular weight of a polymer obtained by polymerizing the monomer component as described above is preferably 1000 or more, more preferably 5000 or more, and from the viewpoint of enhancing the solubility in a solvent, the weight average molecular weight of a polymer is preferably 1000000 or less, more preferably 100000 or less, further preferably 50000 or less. The weight average molecular weight of a polymer can be determined by, for example, gel permeation chromatography.

The material of the substrate includes, for example, glass, polyethylene, polypropylene, polystyrene, polyvinyl chloride, polyamide represented by nylon, polyimide, polyurethane, urea resin, polylactic acid, polyvinyl alcohol, polyvinyl acetate, acrylic resin, polysulfone, polycarbonate, ABS resin, AS resin, silicone resin, ceramic, metal and the like, and the present invention is not limited only to those exemplified ones. Among the substrates made from these materials, a substrate having hydroxyl group on its surface is preferable, and a glass substrate such as a glass plate is more preferable from the viewpoint of securing the polymer firmly to the substrate. When a glass substrate is used as a substrate, it is preferred to previously carry out a UV treatment or an ozone treatment on the glass substrate from the viewpoint of enhancing the adhesion of the polymer.

When a substrate not having hydroxyl group on its surface is used, it is preferred to hydrophilize the surface of a substrate so that hydroxyl group is existed on the surface from the viewpoint of securing the cell culture substrate of the present invention firmly to the substrate. When a substrate made from glass or the like having sufficient hydroxyl groups on its surface is used, it goes without saying that there is no need to make the surface of the substrate hydrophilic so that hydroxyl groups are existed on its surface.

The shape of the substrate cannot be absolutely determined because the shape varies depending on the use of a cell culture substrate and the like. Therefore, it is preferred to appropriately determine the shape in accordance with its use and the like. The shape of the substrate includes, for example, a film, a sheet, a plate, a rod, a molded body formed into a predetermined shape and the like, and the present invention is not limited only to those exemplified ones.

After having formed the coating layer of the polymer on the surface of a substrate, it is preferable to wash the substrate on which the coating layer of the polymer is formed with ethanol, water or the like, and dry the substrate with an inert gas such as nitrogen gas.

The thickness (thickness after drying) of the coating film of the polymer formed on the surface of a material varies depending on the use of a cell culture substrate and the like. Therefore, the thickness cannot be absolutely determined. The thickness of the coating film of the polymer is usually preferably about 10 nm to about 10 μm.

Next, the coating layer of the polymer formed on the surface of the substrate is irradiated at a predetermined position with ion beam, to remove the coating layer of the polymer which has been irradiated with ion beam from the substrate. When the coating layer of the polymer is irradiated with ion beam at a predetermined position, a cell culture substrate having a predetermined pattern of a coating film of the polymer is obtained because the polymer is removed from the position where the ion beam is irradiated.

As the kind of an ion used for the ion beam there can be cited, for example, $H^+$, $Na^+$, $C^+$, $N^+$, $N_2+$, $O_2^+$, $Gd^+$, $He^+$, $Ne^+$, $Ar^+$, $Kr^+$ and the like, and the present invention is not limited only to those exemplified ones.

The exposure of ion beam is preferably $1 \times 10^{13}$ to $1 \times 10^{16}$ ions/cm$^2$ and more preferably $1 \times 10^{13}$ to $1 \times 10^{15}$ ions/cm$^2$ from the viewpoint of manufacturing a cell culture substrate having a predetermined coating pattern of the polymer. It is preferred that the accelerating voltage of the ion beam is usually about 50 to about 200 kV. In addition, it is preferred that the current density of the ion beam is usually 0.5 μA/cm$^2$ or less.

When cells are cultured by using the cell culture substrate from which the coating layer of the polymer has been removed at the predetermined position by the irradiation of ion beam as described above, the cells are cultured at the position where the ion beam is irradiated because the above-mentioned polymer is not existed at the position, and the cells are not cultured at the position where the above-mentioned polymer is existed because the polymer is not irradiated with the ion beam. Therefore, the cells can be cultured in a predetermined shape.

Therefore, according to the method for manufacturing a cell culture substrate of the present invention, there is obtained a cell culture substrate capable of regenerating a cell having a shape corresponding to the shape of a tissue to be regenerated in animals such as human. By using this cell culture substrate, it is possible to culture cells in an arbitrary shape. Therefore, cells can be cultured in a predetermined shape (pattern) by using the cell culture substrate in medical practice such as regenerative medicine.

EXAMPLES

Next, the present invention will be more specifically described by way of examples, but the present invention is not limited only to those examples.

Example 1

A polymerization initiator solution was prepared by dissolving 1.82 g (4 mmol) of (11-(2-bromo-2-methyl)propionyloxy)undecyltrichlorosilane in 15 mL of toluene.

A glass plate (24 mm in length, 12 mm in width, 1 mm in thickness) which had been washed by irradiation with UV and ozone on both surfaces for 1 hour respectively was put in a 100 mL sample bottle, and the polymerization initiator solution obtained in the above was added to the sample bottle so that the glass plate was completely dipped in the solution. After the opening of the sample bottle was sealed with a lid, the sample bottle was allowed to stand for 18 hours at room temperature. Thereafter, the glass plate was taken out from the sample bottle, washed with toluene, and dried in a nitrogen gas stream.

A 100 ml sample bottle was charged with 30.9 mg (0.2143 mmol) of copper bromide, 67.0 mg (0.4286 mmol) of 2,2'-bipyridyl, 1.007 g (4.317 mmol) of N-methacryloyloxyethyl-N,N-dimethylammonium-α-N-methyl-carboxybetaine and 32 μL (0.2143 mmol) of ethyl-2-bromoisobutyrate as a free radical polymerization initiator, and then 10 mL of methanol which had been degassed by argon gas and the glass plate were put into the sample bottle.

Next, the air was removed from the sample bottle by introducing argon gas into the sample bottle. Thereafter, the sample bottle was sealed with a lid, and a polymerization reaction was allowed to start. The polymerization reaction was carried out by allowing the sample bottle to stand for 6 hours at room temperature, and the lid was removed from the sample bottle so that the air was introduced into the sample bottle, to terminate the polymerization reaction. Then, the glass plate was taken out from the sample bottle, washed successively with ethanol and water, and dried with nitrogen gas, to obtain a glass plate having a polymer coating layer formed thereon.

The weight average molecular weight of the polymer obtained in the above was determined in accordance with the following method. Specifically, a 100 ml sample bottle was charged with 30.9 mg (0.2143 mmol) of copper bromide, 67.0 mg (0.4286 mmol) of 2,2'-bipyridyl, 1.007 g (4.317 mmol) of N-methacryloyloxyethyl-N,N-dimethylammonium-α-N-methyl-carboxybetaine and 32 μL (0.2143 mmol) of ethyl-2-bromoisobutyrate as a free radical polymerization initiator, and then 10 mL of methanol which had been degassed with argon gas was put into the sample bottle. Next, the air was removed from the sample bottle by introducing argon gas into the sample bottle. Thereafter, the opening of the sample bottle was sealed with a lid, and a polymerization reaction was allowed to start. The polymerization reaction was carried out by allowing the bottle to stand for 6 hours at room temperature, and the lid was removed from the sample bottle so that the air was introduced into the sample bottle, to terminate the polymerization reaction. The weight average molecular weight of the polymer obtained was found to be 15600 as determined by gel permeation chromatography.

The glass plate on which a coating layer of a polymer obtained in the above was formed was irradiated with ion beam in a heart-like shape of 200 μm in length and 200 μm in width. As the ion beam, $1 \times 10^{14}$ ions/cm$^2$ of Gd$^+$ was irradiated at an accelerating voltage of 50 kV. After the glass plate irradiated with the ion beam was placed in a Petri dish of 35 mm in diameter, 5×10 HEK-293 cells were cultured until 70% confluency in a medium, to which 1% antibiotic was added and which was supplemented with fetal bovine serum (Dulbecco's Modified Eagle Medium with FBS) in this Petri dish at 37° C. in an atmosphere of 5% by volume of carbon dioxide. As a result, the growth of HEK-293 cells was observed only at the portion from which the coating layer had been removed by the irradiation of ion beam.

From the above results, according to Example 1, cells grow only at the portion where a coating layer has been removed from the glass plate when a monomer component containing a nitrogen atom-containing monomer represented by the formula (I) is polymerized, a glass plate is coated with the resulting polymer to form a coating layer of the polymer, the coating layer of the above-mentioned polymer is irradiated with ion beam at the predetermined position, and the coating layer of the polymer irradiated with the ion beam is removed from the glass plate. Therefore, it can be seen that a cell culture substrate capable of culturing cells into an arbitrary shape can be obtained.

Example 2

The same procedure as in Example 1 was carried out except that 0.5035 g (2.159 mmol) of N-methacryloyloxyethyl-N,N-dimethyl-ammonium-α-N-methylcarboxybetaine and 0.2440 g (2.159 mmol) of N-isopropylacrylamide were used in place of 1.007 g (4.317 mmol) of N-methacryloyloxyethyl-N,N-dimethylammonium-α-N-methyl-carboxybetaine in Example 1. As a result, the growth of HEK-293 cells was observed only at the portion from which the coating layer had been removed by the irradiation of ion beam.

From this result, cells grow only at the portion where a coating layer has been removed from the glass plate when a copolymer of N-methacryloyl-oxyethyl-N,N-dimethylammonium-α-N-methylcarboxybetaine and N-isopropylacrylamide is used as a polymer, the coating layer is irradiated with ion beam at a predetermined position in the same manner as in Example 1, and the coating layer of the copolymer irradiated with ion beam is removed from the glass plate. Therefore, it can be seen that a cell culture substrate capable of culturing cells into an arbitrary shape can be obtained.

Example 3

The same procedure as in Example 1 was carried out except that 0.5035 g (2.159 mmol) of N-methacryloyloxyethyl-N,N-dimethylammonium-α-N-methylcarboxybetaine and 0.2807 g (2.159 mmol) of 2-methoxyethyl methacrylate were used in place of 1.007 g (4.317 mmol) of N-methacryloyl-oxyethyl-N,N-dimethylammonium-α-N-methyl-carboxybetaine in Example 1. As a result, the growth of HEK-293 cells was observed only at the portion from which the coating layer had been removed by the irradiation of ion beam.

From this result, cells grow only at the portion where a coating layer has been removed from the glass plate when a copolymer of N-methacryloyloxyethyl-N,N-dimethylammonium-α-N-methylcarboxy-betaine and 2-methoxyethyl methacrylate is used as a polymer, the coating layer is irradiated with ion beam at a predetermined position in the same manner as in Example 1, and the coating layer of the copolymer irradiated with ion beam is removed from the glass plate. Therefore, it can be seen that a cell culture substrate capable of culturing cells into an arbitrary shape can be obtained.

Example 4

The same procedure as in Example 1 was carried out except that 0.5035 g (2.159 mmol) of N-methacrloyloxyethyl-N,N-Dimethyl-ammonium-α-N-methylcarboxybetaine and 0.7211 g (2.159 mmol) of glucosylethyl methacrylate were used in place of 1.007 g (4.317 mmol) of N-methacryloyloxyethyl-N,N-dimethylammonium-α-N-methylcarboxy-betaine in Example 1. As a result, the growth of HEK-293 cells was observed only at the portion from which the coating layer had been removed by the irradiation of ion beam.

From this result, cells grow only at the portion where a coating layer has been removed from the glass plate when a copolymer of N-methacryloyl-oxyethyl-N,N-dimethylammonium-α-N-methylcarboxybetaine and glucosylethyl methacrylate is used as a polymer, the coating layer is irradiated with ion beam at a predetermined position in the same manner as in Example 1, and the coating layer of the copolymer irradiated with ion beam is removed from the glass plate. Therefore, it can be seen that a cell culture substrate capable of culturing cells into an arbitrary shape can be obtained.

Example 5

The same procedure as in Example 1 was carried out except that 0.5035 g (2.159 mmol) of N-methacryloyloxyethyl-N,N-dimethyl-ammonium-α-N-methylcarboxybetaine and 0.5095 g (2.159 mmol) of 2-methacrylolyloxyethyl phosphocholine were used in place of 1.007 g (4.317 mmol) of N-methacryloyloxyethyl-N,N-dimethylammonium-α-N-methyl-carboxybetaine in Example 1. As a result, the growth of HEK-293 cells was observed only at the portion from which the coating layer had been removed by the irradiation of ion beam.

From this result, cells grow only at the portion where a coating layer has been removed from the glass plate when a copolymer of N-methacryloyl-oxyethyl-N,N-dimethylammonium-α-N-methylcarboxybetaine and 2-methacrylolyloxyethyl phosphocholine is used as a polymer, the coating layer is irradiated with ion beam at a predetermined position in the same manner as in Example 1, and the coating layer of the copolymer irradiated with ion beam is removed from the glass plate. Therefore, it can be seen that a cell culture substrate capable of culturing cells into an arbitrary shape can be obtained.

Example 6

The same procedure as in Example 1 was carried out except that 0.5035 g (2.159 mmol) of N-methacryloyloxyethyl-N,N-dimethyl-ammonium-α-N-methylcarboxybetaine and 0.462 g (2.159 mmol) of N-methacryloyloxyethyl-N,N-dimethylammonium-N-propylsulfobetaine were used in place of 1.007 g (4.317 mmol) of N-methacryloyloxyethyl-N,N-dimethylammonium-α-N-methylcarboxybetaine in Example 1. As a result, the growth of HEK-293 cells was observed only at the portion from which the coating layer had been removed by the irradiation of ion beam.

From this result, cells grow only at the portion where a coating layer has been removed from the glass plate when a copolymer of N-methacryloyl-oxyethyl-N,N-dimethylammonium-α-N-methylcarboxybetaine and N-methacryloyloxyethyl-N,N-dimethylammonium-N-propylsulfobetaine is used as a polymer, the coating layer is irradiated with ion beam at a predetermined position in the same manner as in Example 1, and the coating layer of the copolymer irradiated with ion beam is removed from the glass plate. Therefore, it can be seen that a cell culture substrate capable of culturing cells into an arbitrary shape can be obtained.

Comparative Example 1

A 1 L-flask equipped with a nitrogen gas inlet tube, a condenser and a stirrer was charged with 100 g of γ-methacryloyloxypropyl trimethoxysilane (manufactured by Shin-Etsu Chemical Co., Ltd under the trade name of KBM-503) and 400 g of ethyl alcohol. After the pressure in the flask was reduced to degas, nitrogen gas was introduced into the flask to an ordinary pressure.

Next, 10 g of azobisisobutyronitrile was added to the flask, and aging was carried out for 10 hours while maintaining the temperature of the contents in the flask at 80° C. Thereafter, the flask was cooled to 30° C. in a water bath to give a polymer solution. The viscosity average molecular weight of the polymer solution obtained was determined by measuring its viscosity at 25° C. with an Ubbelohde-type viscometer (manufactured by Sogo Laboratory Glass Works Co., Ltd under the type of U-0327-26). As a result, the viscosity average molecular weight was found to be 14000. This polymer solution was used as a resin composition for a cell culture substrate.

Next, a glass substrate (38 mm in length, 26 mm in width and 1 mm in thickness) was washed successively with water, methanol and acetone, and both surfaces of the substrate were subjected to UV irradiation and ozone washing for 1 hour respectively.

The resin composition for a cell culture substrate obtained in the above was diluted with ethyl alcohol to give a solution so that the concentration of the solution was 1% by volume. The substrate was dipped in this solution, and allowed to stand for 10 minutes at room temperature, to form a coating film made of the resin composition for a cell culture substrate on the surface of a substrate, to produce a cell culture substrate.

The cell culture substrate obtained was taken out from the above-mentioned solution, washed with ethyl alcohol and purified water, and dried with nitrogen gas, to obtain a glass plate on which a coating layer of the polymer was formed.

The glass plate on which the coating layer of the polymer was formed in the above was irradiated with ion beam in a heart-like shape, and HEK-293 cells were cultured in the same manner as in Example 1. As a result, the growth of HEK-293 cells was observed not only at the portion from which the coating layer had been removed by the irradiation of ion beam, but also at the portion where the polymer was coated.

From the above results, according to Comparative Example 1, when the coating layer of the polymer irradiated with ion beam was removed, it can be seen that cells cannot be grown up only at the portion from which the coating layer of the polymer has been removed.

INDUSTRIAL APPLICABILITY

According to the method for manufacturing a cell culture substrate of the present invention, there can be provided a cell culture substrate which can regenerate a cell having a shape corresponding to the shape of a tissue to be regenerated. Since cells can be cultured in an arbitrary shape by using this cell culture substrate, it is expected that the cell culture substrate is used in culturing embryonic stem cells (ES cells), mesenchymal cells, induced pluripotent stem cells (iPS cells), progenitor cells and the like in a predetermined shape.

The invention claimed is:

1. A method for manufacturing a cell culture substrate comprising a substrate and a coating layer of a polymer formed on the surface of the substrate, said method comprising the steps of, polymerizing a monomer component comprising a nitrogen atom-containing monomer represented by the formula (I) on the surface of a substrate having hydroxyl groups thereon, to form a coating layer of the polymer on said surface:

[Chem. 1]

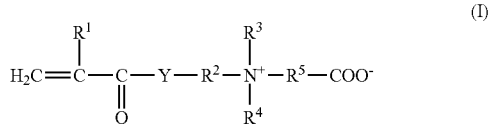

(I)

wherein $R^1$ is hydrogen atom or methyl group, $R^2$ is an alkylene group having 1 to 6 carbon atoms, each of $R^3$ and $R^4$ is independently an alkyl group having 1 to 4 carbon atoms, $R^5$ is an alkylene group having 1 to 4 carbon atoms, and Y is oxygen atom or —NH— group, and irradiating the coating layer of the polymer at a predetermined position with ion beam, to remove the coating layer of the polymer irradiated with the ion beam at the predetermined position.

2. The method for manufacturing a cell culture substrate according to claim 1, wherein the monomer component further comprises at least one copolymerizable monomer selected from the group consisting of an alkyl (meth) acrylamide-based monomer, a polyethylene glycol-based monomer, a polypropylene glycol-based monomer, a sugar backbone-containing monomer, a phosphobetaine-based monomer and a sulfobetaine-based monomer.

3. A cell culture substrate obtained by the method for manufacturing a cell culture substrate according to claim 1.

4. The method for manufacturing a cell culture substrate according to claim 1, wherein the substrate having hydroxyl groups is a glass substrate.

5. The method for manufacturing a cell culture substrate according to claim 4, wherein the glass substrate is a glass plate.

6. The method for manufacturing a cell culture substrate according to claim 1, wherein $R^2$ is a methylene group.

7. The method for manufacturing a cell culture substrate according to claim 1, wherein $R^2$ is an ethylene group.

8. The method for manufacturing a cell culture substrate according to claim 1, wherein $R^3$ and $R^4$ are methyl groups.

9. The method for manufacturing a cell culture substrate according to claim 1, wherein $R^3$ and $R^4$ are ethyl groups.

10. The method for manufacturing a cell culture substrate according to claim 1, wherein $R^5$ is a methylene group.

11. The method for manufacturing a cell culture substrate according to claim 1, wherein $R^5$ is an ethylene group.

* * * * *